(12) United States Patent
Hohmann et al.

(10) Patent No.: US 6,929,781 B1
(45) Date of Patent: Aug. 16, 2005

(54) INTERCONNECTION SUPPORT FOR PLATE-LIKE MICROCOMPONENTS

(75) Inventors: Michael Hohmann, Darmstadt (DE); Michael Schmelz, Griesheim (DE); Hanns Wurziger, Darmstadt (DE); Norbert Schwesinger, Ilmenau (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/856,661

(22) PCT Filed: Nov. 17, 1999

(86) PCT No.: PCT/EP99/08821

§ 371 (c)(1),
(2), (4) Date: Aug. 2, 2001

(87) PCT Pub. No.: WO00/31422

PCT Pub. Date: Jun. 2, 2000

(30) Foreign Application Priority Data

Nov. 24, 1998 (DE) ................................ 198 54 096

(51) Int. Cl.[7] .............................................. B01L 11/00
(52) U.S. Cl. ..................... 422/103; 422/99; 422/100; 422/104; 436/179; 436/180
(58) Field of Search ............. 403/373; 285/124.5; 422/99–104; 361/679; 436/179, 180

(56) References Cited

U.S. PATENT DOCUMENTS

| | | | | |
|---|---|---|---|---|
| 3,631,325 A | * | 12/1971 | Wenz | .......................... 361/705 |
| 4,207,394 A | * | 6/1980 | Aldridge et al. | .............. 435/34 |
| 4,214,292 A | * | 7/1980 | Johnson | ...................... 361/721 |
| 4,315,300 A | * | 2/1982 | Parmerlee et al. | .......... 361/703 |
| 4,322,776 A | * | 3/1982 | Job et al. | ...................... 361/720 |
| 4,445,740 A | * | 5/1984 | Wallace | ........................ 439/152 |
| 4,507,707 A | * | 3/1985 | Willis | .......................... 361/679 |
| 4,731,698 A | * | 3/1988 | Millot et al. | ................. 361/704 |
| 4,889,613 A | * | 12/1989 | McNeal et al. | ............. 204/416 |
| 4,940,527 A | * | 7/1990 | Kazlauskas et al. | ........ 204/401 |
| 4,985,129 A | * | 1/1991 | Burd | ........................... 204/603 |
| 5,236,668 A | * | 8/1993 | Higdon | ......................... 422/89 |
| 5,279,796 A | * | 1/1994 | Parker et al. | ................ 422/100 |
| 5,519,635 A | | 5/1996 | Miyake | |
| 5,603,351 A | * | 2/1997 | Cherukuri et al. | .......... 137/597 |
| 5,746,976 A | * | 5/1998 | Yamada et al. | ................ 422/62 |
| 6,001,233 A | * | 12/1999 | Levy | ........................... 204/618 |
| 6,193,868 B1 | * | 2/2001 | Hsu | ............................ 204/618 |
| 6,349,039 B1 | * | 2/2002 | Boe | ............................ 361/801 |
| 6,399,023 B1 | * | 6/2002 | Chow | ........................... 422/81 |
| 6,399,394 B1 | * | 6/2002 | Dahm et al. | ................. 436/180 |
| 6,692,697 B1 | * | 2/2004 | Melendez et al. | ............ 422/57 |

FOREIGN PATENT DOCUMENTS

| | | | | |
|---|---|---|---|---|
| DE | 19746585 | | 4/1999 | |
| EP | 040186 | | 11/1981 | |
| WO | WO 9838487 A2 | * | 9/1998 | ............ G01N 1/31 |

* cited by examiner

Primary Examiner—Jili Warden
Assistant Examiner—Dwayne K Handy
(74) Attorney, Agent, or Firm—Millen, White, Zelano & Branigan, P.C.

(57) ABSTRACT

An interconnection support for plate-like microcomponents (1) has a support rail (2) which is attached to a support plate (3). An insertion slot (4) for the support rail (2) accommodates an insertion edge (5) of a plate-like microcomponent (1). Like connections (10, 10a), which can be connected to associated connections (11) in an outside (1a) of the plate-like microcomponent (1), are provided in at least one side wall (9) of the insertion slot (4) of the support rail (2).

Figure 1:
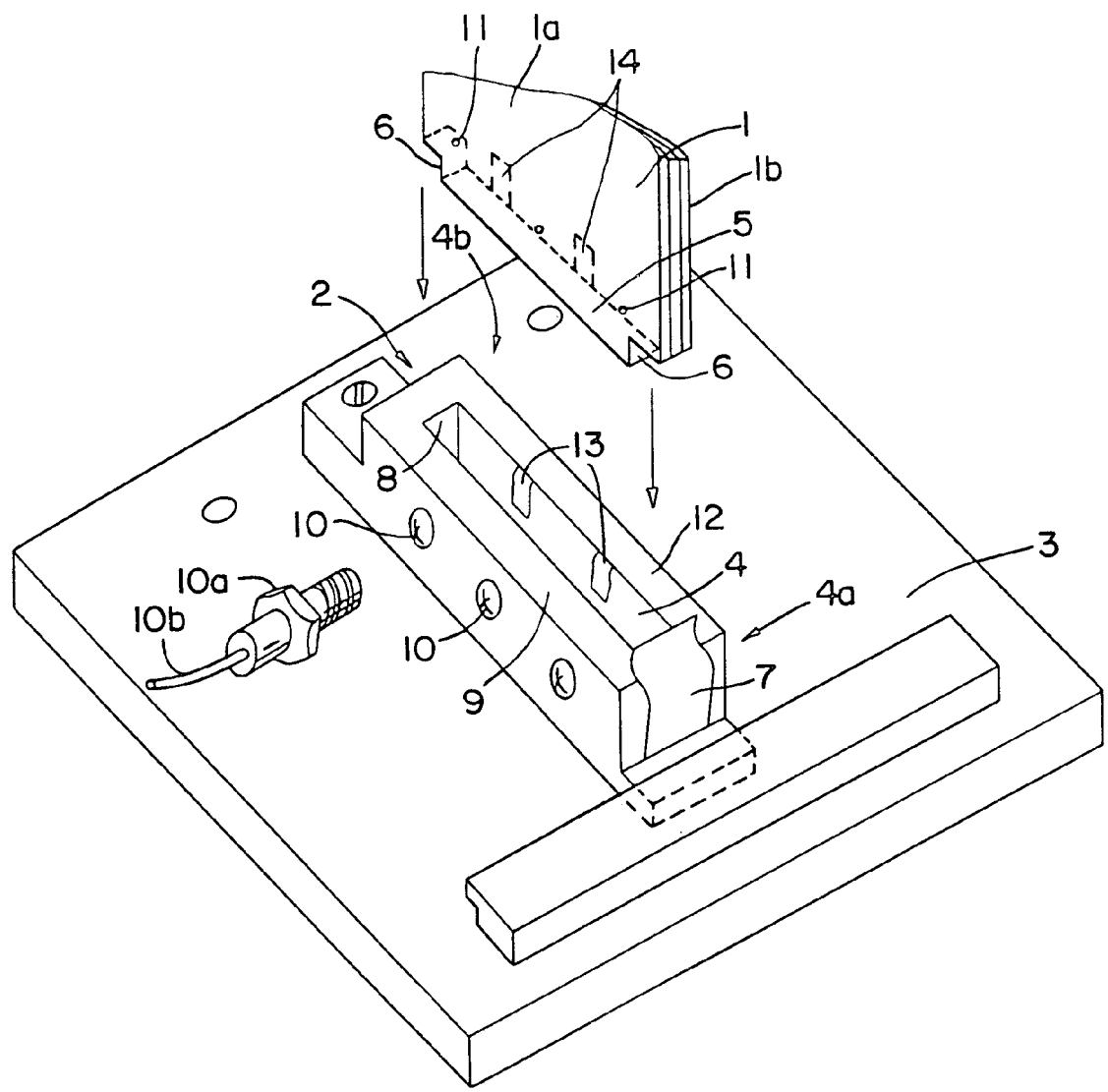

14 Claims, 3 Drawing Sheets ns of the microcomponent 1 and are each intended for the accommodation of a screw connection 10a, through which liquid or gaseous substances are fed to or discharged from the microcomponent 1 via fluid lines 10b, are provided in one side wall 9 of the insertion slot 4. After insertion of the microcomponent 1 into the insertion slot 4, the screw connections are screwed against the microcomponent 1 and thus pressed against substantially flush fluid connections 11 in the outside surface 1a through the insertion edge portion 5 of the plate-like microcomponent in a leak-proof manner.

INTERCONNECTION SUPPORT FOR PLATE-LIKE MICROCOMPONENTS

The invention relates to an interconnection support for plate-like microcomponents.

Plate-like microcomponents, such as micromixers, micropumps, microvalves or the like, serve for carrying out chemical reactions with extremely small mass flow rates. The use of microcomponents enables precise temperature control and good mixing, enabling significantly more accurate process control at the same time as increased safety.

The microcomponents usually consist of a plurality of plane-parallel plates lying one on top of the other which contain structures in their surfaces lying one on top of the other which are necessary for the requisite function. Owing to good thermal conductivity and structurability, these plates usually consist of silicon (silicon wafers) which contain in the interior a geometry matched to the function of the microcomponent. However, it is also possible to use other, chemically resistant materials matched to the use conditions.

Hitherto, primarily individual microcomponents, usually with a plate-like design, have been employed and in each case provided individually with the inlet and outlet lines for liquid and gaseous components and—if necessary—with electrical connections. However, an essential aspect of the use of such microcomponents is connection to standard laboratory equipment so that the advantages of microsystems can be employed on a laboratory scale.

The object of the invention is therefore to provide an interface between microtechnology and laboratory technology via which the microsystems can be adapted reliably and simply to standard laboratory equipment.

This object is achieved in accordance with the invention by an interconnection support for plate-like microcomponents having at least one support rail which is attached to a support plate and which has an insertion slot for the accommodation of an insertion edge of a plate-like microcomponent, with line connections which can be connected to associated connections in at least one outside of the plate-like microcomponent being provided in at least one of the two side walls of the insertion slot of the support rail.

With this interconnection support, a mechanically stable mount is also created at the same time as a connection system. The connection system enables supply with reagents and the implementation of an electrical connection, for example for measurement technology, heating, cooling, etc. The microcomponents can be connected in a simple manner and exchanged easily. The use of a plurality of support rails on a common support plate makes it possible to achieve spatially compact accommodation of a plurality of plate-like microcomponents. Universal connection technology of this type enables mechanically stable construction of microsystems with standardized supply technology in an extremely small space.

According to a preferred embodiment of the invention, it is provided that at least one of the side walls of the insertion slot has at least one threaded hole for the accommodation of a screw connection, which can be screwed against the associated outside of the plate-like microcomponent. This simultaneously achieves leak-proof connection of the microcomponent to the screw connection and at the same time reliable fixing of the plate-like microcomponent in the support rail.

In order to ensure precise and reliable alignment of the plate-like microcomponent in the support rail, it is provided, in a further embodiment of the inventive idea, that, at one end of the insertion slot, a spring is arranged which acts in the longitudinal direction of the slot and by means of which the plate-like microcomponent can be pressed against a centring stop at the other end of the insertion slot.

Electrical contact surfaces which can be brought into contact with associated electrical contacts of the plate-like microcomponent are arranged between the threaded holes or in the opposite side wall of the insertion slot. An electrical connection as is in many cases necessary for measurement sensors in the microcomponent, for heating, cooling or similar purposes, is thus formed at the same time.

In a further refinement of the inventive idea, it may be provided that the support rail is connected to a connection rail which extends perpendicular to the support plate and has an insertion slot for the accommodation of a further insertion edge of the plate-like microcomponent, with line connections which can be connected to associated connections in at least one outside of the plate-like microcomponent being provided in at least one of the two side walls of the insertion slot of the connection rail.

The connection rail rising vertically from the support rail offers firstly the possibility of providing further line connections there; secondly, this connection rail forms a stable mount for the inserted plate-like microcomponent, enabling other mounts and fixings to be omitted.

Further advantageous embodiments of the inventive idea are the subject-matter of further sub-claims.

Figure 2:
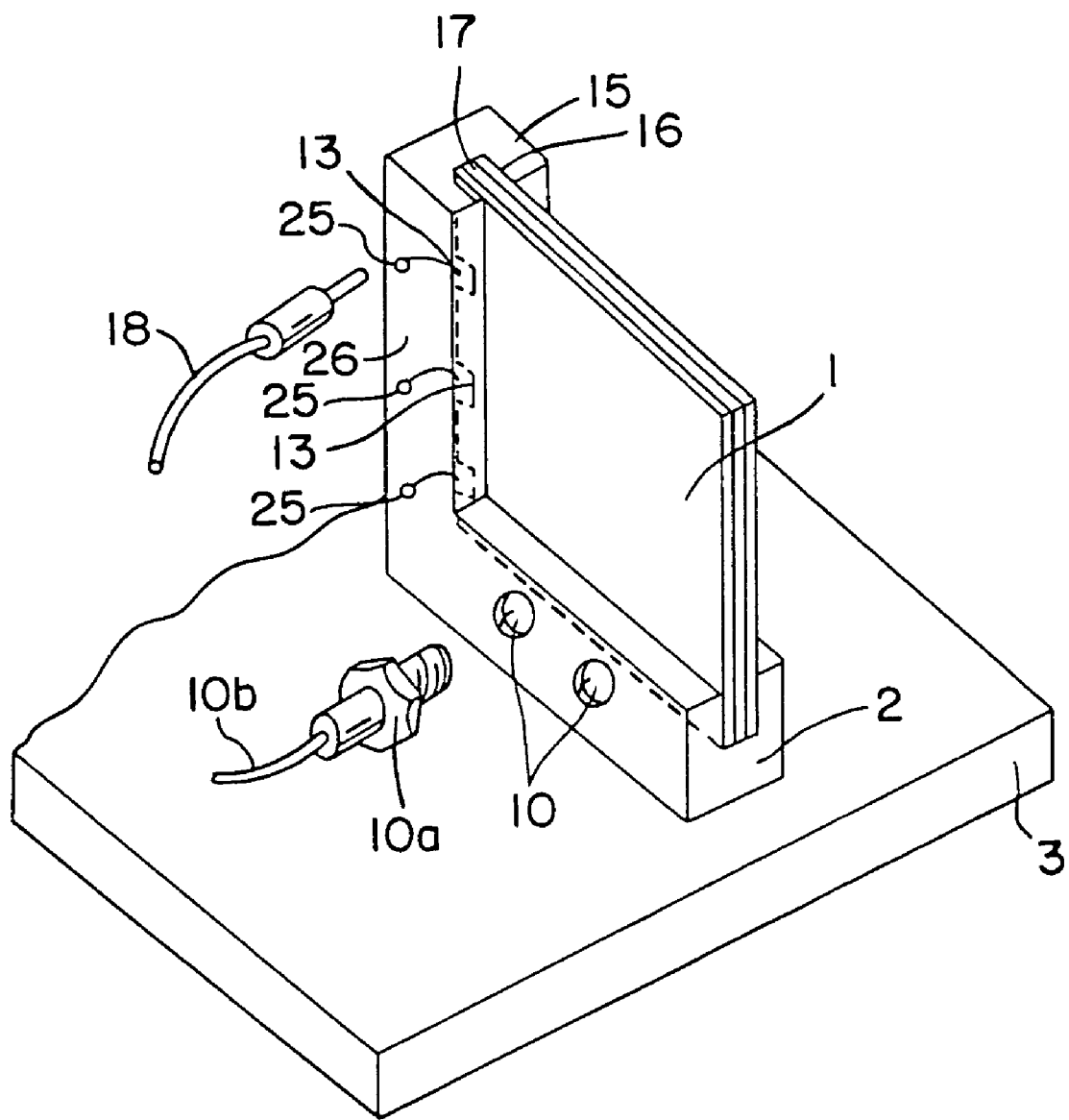
Figure 3:
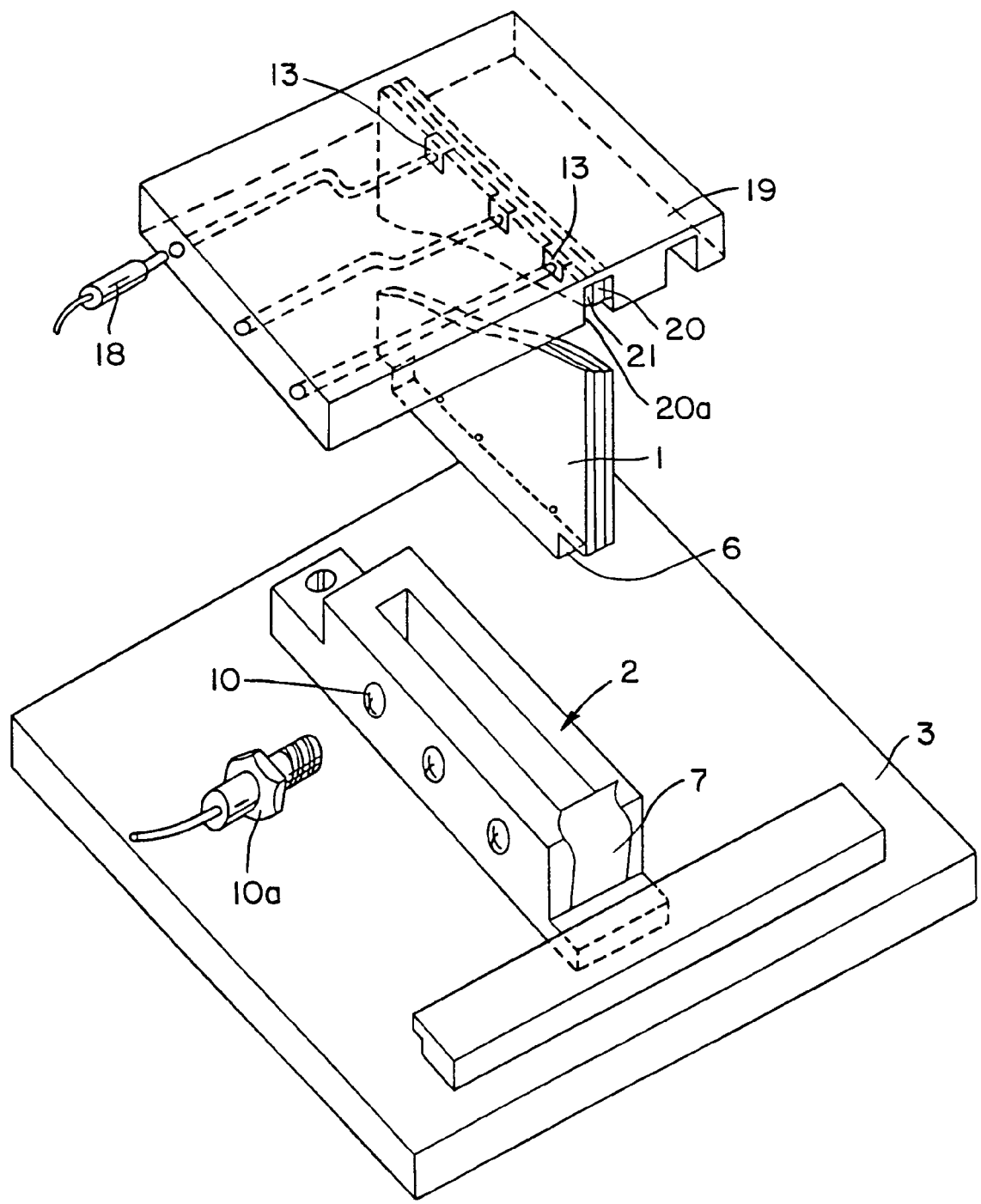

Illustrative embodiments of the invention are explained below in greater detail and are shown in the drawing, in which, in each case in perspective view:

FIG. 1 shows an interconnection support for plate-like microcomponents with a support rail attached to a support plate, FIG. 2 shows an interconnection support with additional connection rail, and FIG. 3 shows an interconnection support with a connection holder separated from the support rail.

The interconnection support shown in FIG. 1 serves for the accommodation of a plate-like microcomponent 1. A support rail 2, consisting, for example, of plastic, is attached to a support plate 3. The support rail 2 has a longitudinally extending insertion slot 4, into which the plate-like microcomponent 1 can be inserted by means of a base strip 5. The base strip 5 is limited by lateral cut-outs 6, which butt against the ends of the insertion slot 4 and thus ensure precise definition of the insertion depth. The slot 4 unobstructed and is defined by a pair of planar side walls.

A spring 7, for example a leaf spring, which acts in the longitudinal direction of the insertion slot 4, is arranged at one end 4a of the slot and presses the base 5 of the plate-like microcomponent 1 against a centring stop 8 at the other end 4b of the insertion slot 4.

A plurality of threaded holes 10 which extend transversely to the plane of the plate-like microcomponent 1 and are each intended for the accommodation of a screw connection 10a, through which liquid or gaseous substances are fed to or discharged from the microcomponent 1 via fluid lines 10b, are provided in one side wall 9 of the insertion slot 4. After insertion of the microcomponent 1 into the insertion slot 4, the screw connections are screwed against the microcomponent 1 and thus pressed against substantially flush fluid connections 11 in the outside surface 1a through the insertion edge portion 5 of the plate-like microcomponent in a leak-proof manner.

Electrical contact surfaces 13, for example contact springs, are arranged in the side wall 12 of the insertion slot 4 which is opposite the side wall 9 and come into contact with associated electrical contacts 14 on the facing outer surface 1b after insertion of the microcomponent 1 and serve for electrical connection.

The illustrative embodiment in accordance with FIG. 2 differs from the illustrative embodiment in accordance with FIG. 1 essentially through the fact that the support rail 2 is connected to a connection rail 15 which extends perpendicular to the support plate 3 and likewise has an insertion slot 16 for the accommodation of a further insertion edge 17 of the plate-like microcomponent 1.

In the illustrative embodiment in accordance with FIG. 2, only the threaded holes 10 for the accommodation of the screw connections 10a provided in the support rail 2 connected to the support plate 3. The electrical contact surfaces 13 described are only arranged in the connection rail 15 and serve for the connection of electrical leads 18 to associated connections (25) in at least one outside surface 26.

The illustrative embodiment in accordance with FIG. 3 differs from the illustrative embodiments described above essentially through the fact that a connection holder 19, which is separated from the support rail 2, which again has only the threaded holes 10 here, has an accommodation slot 20 for an edge 21 of the plate-like microcomponent 1. The electrical contact surfaces 13, which are in contact with the associated contacts 14 of the plate-like microcomponent 1, are arranged in the first side wall 20a of the accommodation slot 20.

The connection holder 19, which may also be connected or attached to the support plate 3 in a suitable manner, additionally fixes the accommodated microcomponent 1 or a plurality of such accommodated microcomponents 1.

In all the illustrative embodiments shown, a plurality of microcomponents 1 can be accommodated by the arrangement of a plurality of support rails 2 on a common support plate 3. Thus, multistep or even parallel reactions can be carried out in an extremely small space by connecting a plurality of microcomponents 1 in series.

What is claimed is:

1. An interconnection support for plate-like micro-components (1) constructed and arranged for receiving fluid material to carry out chemical reactions, the interconnection support having at least one support rail (2) on the interconnection support which is attached to a support plate (3) and which has an unobstructed insertion slot (4) defined by planar side walls (9 and 12) for the accommodation of at least a first insertion edge portion (5) of a plate-like microcomponent (1), wherein the edge portion (5) has substantially flush fluid connections (11) therein, the interconnection support having fluid line connections (10) opening within the insertion slot 4, the fluid line connections 10 being constructed and arranged to be connected to the associated flush fluid connections (11) through at least one outside surface (1a, 1b) of the plate-like microcomponent (1) to transfer fluid materials to and from the plate-like microcomponent, the fluid line connections being provided in at least one of the two planar side walls (9, 12) of the insertion slot (4) of the support rail (2) whereby the unobstructed insertion slot (4) and flush fluid connections (11) facilitate sliding the first insertion edge portion (5) of the plate-like microcomponents (1) into the slot (4).

2. The interconnection support according to claim 1, wherein the fluid connections of the at least one of the side walls (9) of the insertion slot (4) comprises at least one threaded hole (10) therethrough for the accommodation of a threaded fluid coupling (10a) to couple a fluid line 10b to the hole 10 that is screwed against the associated outside surface (1a) of the plate-like microcomponent (1) adjacent to the associated flush fluid connection (11) in the microcomponent (1).

3. The interconnection support according to claim 1, wherein, at a first end (4a) of the insertion slot (4), a spring (7) is arranged which acts in the longitudinal direction of the slot allowing the plate-like microcomponent (1) to be pressed against a centering stop (8) at a second end (4b) of the insertion slot (4).

4. The interconnection support according to claim 2, further including electrical contact surfaces (13) constructed and arranged to be brought into contact with associated electrical contacts (14) of the plate-like microcomponent (1), the electrical contact being arranged between the threaded holes (10) in an opposed side wall (9) of the insertion slot (4).

5. The interconnection support according to claim 1, wherein the support rail (2) is connected to a connection rail (15) which extends perpendicular to the support plate (3) and has an insertion slot (16) for the accommodation of a second insertion edge (17) of the plate-like microcomponent (1), wherein line connections (13) for electrical lines (18) are connected to associated connections (25) in at least one outside surface (26) of the plate-like microcomponent (1) that are provided in at least one of two side walls defining the insertion slot (16) of the connection rail (15).

6. The interconnection support according to claim 5, wherein the support rail (2) has more than one threaded hole (10) for the accommodation of more than one threaded fluid connection (10a), and wherein the connection rail (15) has electrical contact surfaces (13) thereon.

7. The interconnection support according to claim 1, wherein a connection holder (19) which is separate from the support rail (2) has an accommodation slot (20) for an insertion edge (21) of the plate-like microcomponent (1) disposed opposite the first insertion edge, and wherein electrical contact surfaces (13), which are brought into contact with associated contacts of the plate-like microcomponent, are arranged in at least one side wall (20a) of the accommodation slot (20).

8. The interconnection support of claim 1 wherein the plate-like microcomponents comprise plane-parallel plates superimposed on one another, the plane parallel plates having surface structures providing space for chemical reactions.

9. In combination, an interconnection support and at least one plate-like microcomponent, the plate-like microcomponent having plane-parallel plates superimposed on one another and defining surface structures providing space for chemical reactions; the combination comprising:

an interconnection support for the plate-like micro-components being constructed and arranged for receiving fluid material, the interconnection support having at least one support rail (2) on the interconnection support which is attached to a support plate (3) and which has an unobstructed insertion slot (4) with planar walls (9 and 12) for the accommodation of at least a first insertion edge portion (5) of a plate-like microcomponent (1), wherein the edge portion has a substantially flush fluid connections (11) therein, the interconnection support having fluid line connections (10) opening within the unobstructed slot, for connection to associated substantially flush fluid connections (11) through at least one outside surface (1a, 1b) of the plate-like microcomponent (1) to transmit fluid materials into and out of the plate-like microcomponent, the fluid line connections being provided in at least one of the two side walls (9, 12) of the insertion slot (4) of the support rail (2); and at least one of the planar side walls (9 and 12) of the insertion slot (4) having at least one threaded hole (10) therethrough for the accommodation of a threaded a fluid coupling (10a) to couple a fluid line (10b) to the hole 10 that is screwed against the associated outside surface (1a) of the plate-like microcomponent (1) to fluidly connect with the associated substantially flush fluid connection 11 in the microcomponent (1).

10. The combination according to claim 9 wherein at a first end (4a) of the insertion slot (4), a spring (7) is arranged which acts in the longitudinal direction of the slot allowing the plate-like microcomponent (1) to be pressed against a centering stop (8) at a second end (4b) of the unobstructed insertion slot (4).

11. The combination according to claim 10, further including electrical contact surfaces (13), constructed and arranged to be brought into contact with associated electrical contacts (14) of the plate-like microcomponent (1), the electrical contacts being disposed between holes (10) in an opposed side wall 9 of the insertion slot (4).

12. The combination according to claim 10, wherein the support rail (2) is connected to a connection rail (15) which extends perpendicular to the support plate (3) and has an insertion slot (16) for the accommodation of a second insertion edge (17) of the plate-like microcomponent (1), wherein line connections (13) for electrical lines (18) are connected to associated connections (25) in at least one outside surface (26) of the plate-like microcomponent (1) that are provided in at least one of two side walls defining the insertion slot (16) of the connection rail (15).

13. The combination according to claim 12, wherein the support rail (2) has more than one threaded hole (10) for the accommodation of more than one screw connection (10a), and wherein the connection rail (15) has electrical contact surfaces (13) thereon.

14. The combination according to claim 13, wherein a connection holder (19) which is separate from the support rail (2) has an accommodation slot (20) for an insertion edge (21) of the plate-like microcomponent (1) disposed opposite the first insertion edge, and wherein electrical contact surfaces (13), which are brought into contact with associated contacts of the plate-like microcomponent, are arranged in at least one side wall (20a) of the accommodation slot (20).

* * * * *

UNITED STATES PATENT AND TRADEMARK OFFICE
CERTIFICATE OF CORRECTION

PATENT NO. : 6,929,781 B1
DATED : August 16, 2005
INVENTOR(S) : Michael Hohmann et al.

It is certified that error appears in the above-identified patent and that said Letters Patent is hereby corrected as shown below:

Column 3,
Line 51, reads "connections 10" should read -- connections (10) --.
Line 66, reads "fluid line 10b" should read -- fluid line (10b) --.
Line 67, reads "hole 10" should read -- hole (10) --.

Column 4,
Line 44, reads "plane parallel" should read -- plane-parallel --.
Line 60, reads "has a substantially" should read -- has substantially --.

Column 5,
Line 8, reads "hole 10" should read -- hole (10) --.
Line 11, reads "connection 11" should read -- connection (11) --.
Line 23, reads "side wall 9" should read -- side wall (9) --.

Signed and Sealed this

Twenty-first Day of March, 2006

JON W. DUDAS
*Director of the United States Patent and Trademark Office*